(12) United States Patent
Bakthavatchalam et al.

(10) Patent No.: US 6,589,952 B2
(45) Date of Patent: Jul. 8, 2003

(54) IMIDAZO[1,2-A]PYRAZINES FOR THE TREATMENT OF NEUROLOGICAL DISORDERS

(75) Inventors: Rajagopal Bakthavatchalam, Branford, CT (US); Richard G. Wilde, Newark, DE (US); Paul J. Gilligan, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/905,097

(22) Filed: Jul. 13, 2001

(65) Prior Publication Data

US 2002/0049208 A1 Apr. 25, 2002

Related U.S. Application Data

(60) Provisional application No. 60/218,339, filed on Jul. 14, 2000.

(51) Int. Cl.[7] .................. C07D 487/04; A61K 31/4985; A61P 3/04; A61P 25/22; A61P 25/24
(52) U.S. Cl. ........................................ 514/249; 540/350
(58) Field of Search ........................... 514/249; 540/350

(56) References Cited

U.S. PATENT DOCUMENTS 5,236,901 A * 8/1993 Burks et al. .................. 514/21

FOREIGN PATENT DOCUMENTS

| WO | WO 95/10506 | 4/1995 |
|---|---|---|
| WO | WO 97/35539 | 10/1997 |
| WO | WO 97/35846 | 10/1997 |
| WO | WO 97/44308 | 11/1997 |
| WO | WO 98/03510 | 1/1998 |
| WO | WO 99/01439 | 1/1999 |
| WO | WO 99/01454 | 1/1999 |
| WO | WO 99/11643 | 3/1999 |
| WO | WO 99/51608 | 10/1999 |
| WO | WO 00/01675 | 1/2000 |

OTHER PUBLICATIONS

Stratakis, "Endocrinology: Basic and Clinical Principles" (Humana Press, 1997) pp. 185–209.*
Chalmers TiPS 17, 166–172 (1998).*
Jones et al, "British Society of Gastroenterology guidelines for the management of the irritable bowel syndrome." Gut 2000, (Suppl II)47:ii1–ii19.*
L. K. McLoon et al, Abstract of Inflammation Research vol. 51 Issue 1 (2002), pp 16–23.*
Catherine Rivier, Frontiers in Bioscience 4, d514–519, Jun. 1, 1999.*
XERECEPT™ Product report http://www.ntii.com/products/xerecept.shtml.*
Search for Novel Corticotropin–Releasing Factor Analogs of Potential Therapeutic Utility in Alzheimer's Disease http://www.crdf.org/Abstracts/fund/RB1161.html.*

M. Leonhardt et al Abstract of European Journal of Nutrition vol. 38 Issue 1 (1999) pp 1–13.*
J. Rivier et al., Proc. Nat. Acad. Sci. (USA), 80:4851 (1983).
W. Vale et al., Science, 213:1394 (1981).
W. Vale et al., Rec. Prog. Horm. Res., 39:245 (1983).
G.F. Koob, Persp. Behav. Med., 2:39 (1985).
E.B. DeSouza et al., J. Neurosci., 5:3189 (1985).
J.E. Blalock, Physiological Reviews, 69:1 (1989).
J.E. Morley, Life Sci., 41:527 (1987).
E.B. DeSouza, Hosp. Practice, 23:59 (1988).
C.B. Nemeroff et al., Science, 226:1342 (1984).
C.M. Banki et al., Am. J. Psychiatry, 144:873 (1987).
R.D. France et al., Biol. Psychiatry, 23:86 (1988).
M. Arato et al., Biol. Psychiatry, 25:355 (1989).
C.B. Nemeroff et al., Arch. Gen. Psychiatry, 45:577 (1988).
P.W. Gold et al., Am. J. Psychiatry, 141:619 (1984).
F. Holsboer et al., Psychoneuroendocrinology, 9:147 (1984).
P.W. Gold et al., New Eng. J. Med., 314:1129 (1986).
R.M. Sapolsky, Arch. Gen. Psychiatry, 46:1047 (1989).

(List continued on next page.)

Primary Examiner—Mark L. Berch
(74) Attorney, Agent, or Firm—Shah Makujina; Kenneth B. Rubin; Woodcock Washburn LLP

(57) ABSTRACT

Provided herein are novel imidazo[1,2-a]pyrazines of Formula I:

$$\text{Formula I}$$

wherein:
  X is $CHR^5$, $NR^5$, O, S, $S(O)_n$ or a single bond, wherein n is equal to 0, 1 or 2;
  D is aryl or heteroaryl attached through an unsaturated carbon atom and wherein said aryl or heteroaryl is optionally substituted at any available position with from 1–5 of $A^1$, $A^2$, $A^3$, $A^4$ and $A^5$;
  $R^2$ is $C_{1-4}$ alkyl or $C_{3-8}$ cycloalkyl, each of which is optionally substituted with from 1–3 hydroxy, halogen or $C_{1-4}$ alkoxy, or wherein when X is a bond, $R^2$ is optionally also CN, $CF_3$, $C_2F_5$, $C_{1-4}$ alkyl or $C_{3-8}$ cycloalkyl, each of which $C_{1-4}$ alkyl or $C_{3-8}$ cycloalkyl is optionally substituted with from 1–3 hydroxy, halogen and $C_{1-4}$ alkoxy;
as well as compositions containing the same, useful in the treatment of, for example, neurological and psychological disorders characterized by corticotropin releasing factor (CRF) overexpression.

22 Claims, No Drawings

OTHER PUBLICATIONS

Grigoriadis et al., Neuropsychopharmacology, 2:53 (1989).
D.R. Britton et al., Life Sci., 31:363 (1982).
C.W. Berridge and A.J. Dunn Regul. Peptides, 16:83 (1986).
C.W. Berridge and A.J. Dunn, Horm. Behav., 21:393 (1987).
Dunn, Brain Research Reviews, 15:71 (1990).
K.T. Britton et al., Psychopharmacology, 86:170 (1985).
K.T. Britton et al., Psychopharmacology, 94:306 (1988).
N.R. Swerdlow et al., Psychopharmacology, 88:147 (1986).
G.F. Koob and K.T. Britton, Corticotropin–Releasing Factor: Basic and Clinical Studies of a Neuropeptide, E.B. DeSouza and C.B. Nemeroff eds., CRC Press, p221 (1990).

* cited by examiner

IMIDAZO[1,2-A]PYRAZINES FOR THE TREATMENT OF NEUROLOGICAL DISORDERS

CROSS-REFERENCE TO RELATED APPLICATIONS

This application claims the benefit of U.S. Provisional Application No. 60/218,339, filed Jul. 14, 2000.

FIELD OF THE INVENTION

This invention relates to compounds which are novel imidazo[1,2-a]pyrazines, and to the use of such compounds as CRF receptor antagonists in the treatment of various neurological disorders.

BACKGROUND OF THE INVENTION

Corticotropin releasing factor (herein referred to as CRF), a 41 amino acid peptide, is the primary physiological regulator of proopiomelanocortin (POMC)—derived peptide secretion from the anterior pituitary gland [J. Rivier et al., *Proc. Nat. Acad. Sci. (USA)* 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

It has also been postulated that CRF has a role in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

It has been further postulated that CRF has a role in immunological, cardiovascular or heart-related diseases such as hypertension, tachycardia and congestive heart failure, stroke, osteoporosis, premature birth, psychosocial dwarfism, stress-induced fever, ulcer, diarrhea, postoperative ileus and colonic hypersensitivity associated with psychopathological disturbance and stress.

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical CRF9-41) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

The following publications each describe CRF antagonist compounds; however, none disclose the compounds provided herein: WO95/10506; WO99/51608; WO97/35539; WO99/01439; WO97/44308; WO97/35846; WO98/03510; WO99/11643; PCT/US99/18707; WO99/01454; and, WO00/01675.

SUMMARY OF THE INVENTION

This invention provides a compound of the Formula (I):

(I)

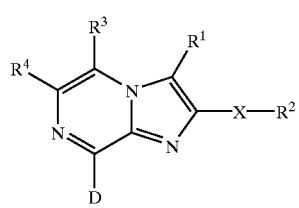

wherein: X is CHR$^5$, NR$^5$, O, S, S(O)$_n$ or a single bond, wherein n is equal to 0, 1 or 2; D is aryl or heteroaryl attached through an unsaturated carbon atom and wherein said aryl or heteroaryl is optionally substituted with from 1–5 A$^1$–A$^5$; R$^1$ is C$_{1-10}$ alkyl, C$_{2-10}$ alkenyl, C$_{2-10}$ alkynyl, C$_{3-8}$ cycloalkyl, C$_{4-12}$ cycloalkylalkyl, NR$^6$R$^7$ or —C(R$^8$)(R$^9$)—O—R$^{10}$; R$^2$ is C$_{1-4}$ alkyl or C$_{3-8}$ cycloalkyl, each of which is optionally substituted with from 1–3 hydroxy, halogen or C$_{1-4}$ alkoxy, or wherein when X is a bond, R$^2$ is optionally also CN, CF$_3$, C$_2$F$_5$, C$_{1-4}$ alkyl or C$_{3-8}$ cycloalkyl, each of which C$_{1-4}$ alkyl or C$_{3-8}$ cycloalkyl is optionally substituted with from 1–3 hydroxy, halogen and C$_{1-4}$ alkoxy; R$^3$ and R$^4$ are selected independently from H, C$_{1-4}$ alkyl, C$_{2-4}$ alkenyl, C$_{2-4}$ alkynyl, C$_{3-5}$ cycloalkyl, C$_{1-4}$ alkoxy, C$_{1-4}$ haloalkyl, C$_{1-4}$ haloalkoxy, halogen, CN, or NR$^6$R$^7$; R$^5$ is H, C$_{1-4}$ alkyl or C$_{3-8}$ cycloalkyl; R$^6$ and R$^7$ are each independently H, C$_{1-4}$ alkyl, C$_{1-4}$ haloalkyl, C$_{2-8}$ alkoxyalkyl, C$_{3-6}$ cycloalkyl, C$_{4-12}$ cycloalkylalk aryl, aryl(C$_{1-4}$ alkyl)-, heteroaryl or heteroaryl(C$_{1-4}$ alkyl)-; R$^8$ and R$^9$ are each independently H or C$_{1-4}$ alkyl, or R$^8$ and R$^9$ are taken together as =CH$_2$, C$_{2-4}$ alkenyl, C$_{2-4}$ alkynyl; and, R$^{10}$ is H or C$_{1-4}$ alkyl. Preferred embodiments of this invention are set forth hereinbelow.

Said compounds antagonize CRF receptors, that is, they bind to the receptors such that CRF is inhibited from binding to the antagonized receptors. The compounds of this invention are thus useful as therapeutic agents in conditions characterized by excessive CRF expression, and this invention thus provides methods of treating a subject afflicted with a disorder, e.g., an anxiety- or depression-related disorder, characterized by CRF overexpression.

DETAILED DESCRIPTION OF THE INVENTION

This invention provides a compound of the Formula (I):

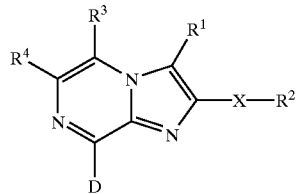

(I)

wherein the various substituents are as described hereinbelow.

R$^1$ is C$_{1-10}$ alkyl, C$_{2-10}$ alkenyl, C$_{2-10}$ alkynyl, C$_{3-8}$ cycloalkyl, C$_{4-12}$ cycloalkylalkyl, NR$^6$R$^7$ or —C(R$^8$)(R$^9$)—O—R$^{10}$. R$^2$ is C$_{1-4}$ alkyl or C$_{3-8}$ cycloalkyl, each of which is optionally substituted with from 1–3 hydroxy, halogen or C$_{1-4}$ alkoxy, or wherein when X is a bond, R$^2$ is optionally also CN, CF$_3$, C$_2$F$_5$, C$_{1-4}$ alkyl or C$_{3-8}$ cycloalkyl, each of which C$_{1-4}$ alkyl or C$_{3-8}$ cycloalkyl is optionally substituted with from 1–3 hydroxy, halogen and C$_{1-4}$ alkoxy. R$^3$ and R$^4$ are each selected independently from H, C$_{1-4}$ alkyl, C$_{2-4}$ alkenyl, C$_{2-4}$ alkynyl, C$_{3-5}$ cycloalkyl, C$_{1-4}$ alkoxy, C$_{1-4}$ haloalkyl, C$_{1-4}$ haloalkoxy, halogen, CN, or NR$^6$R$^7$. R$^5$ is H, C$_{1-4}$ alkyl or C$_{3-8}$ cycloalkyl. R$^6$ and R$^7$ are each independently H, C$_{1-4}$ alkyl, C$_{1-4}$ haloalkyl, C$_{2-8}$ alkoxyalkyl, C$_{3-6}$ cycloalkyl, C$_{4-12}$ cycloalkylalkyl, aryl, aryl(C$_{1-4}$ alkyl)-, heteroaryl or heteroaryl(C$_{1-4}$ alkyl)-. R$^8$ and R$^9$ are each independently H or C$_{1-4}$ alkyl, or R$^8$ and R$^9$ are taken together as =CH$_2$, C$_{2-4}$ alkenyl, C$_{2-4}$ alkynyl. R$^{10}$ is H or C$_{1-4}$ alkyl. R$^{11}$ is H, C$_{1-4}$ alkyl, C$_{3-7}$ cycloalkyl, C$_{4-12}$ cycloalkylalkyl, phenyl or benzyl, each phenyl or benzyl optionally substituted on the aryl moiety with 1–3 groups of C$_{1-4}$ alkyl, halogen, C$_{1-4}$ haloalkyl, nitro, C$_{1-4}$ alkoxy, C$_{1-4}$ haloalkoxy, or dimethylamino. R$^{12}$, R$^{13}$ and R$^{14}$ are each independently H, C$_{1-6}$ alkyl, C$_{3-10}$ cycloalkyl, C$_{4-16}$ cycloalkylalkyl or C$_{1-4}$ haloalkyl.

X is CHR$^5$, NR$^5$, O, S, S(O)$_n$ or a single bond, wherein n is equal to 0, 1 or 2. D is aryl or heteroaryl attached through an unsaturated carbon atom, wherein said aryl is optionally substituted at any available position with from 1–5 of, and said heteroaryl is optionally substituted with from 1–4 of, A$^1$, A$^2$, A$^3$, A$^4$ and A$^5$. A$^1$, A$^2$, A$^3$, A$^4$ and A$^5$ are each independently H, C$_{1-6}$ alkyl, C$_{3-6}$ cycloalkyl, halo, C$_{1-4}$ haloalkyl, cyano, nitro, —OR$^{12}$, SH, —S(O)$_n$R$^{13}$, —COR$^{12}$, —CO$_2$R$^{12}$, —OC(O)R$^{13}$, —NR$^{11}$COR$^{12}$, —N(COR$^{12}$)$_2$, —NR$^{11}$CONR$^{12}$R$^{14}$, or wherein A$^1$, A$^2$, A$^3$, A$^4$ and A$^5$ are each independently phenyl or phenyl substituted with from 1 to 4 of C$_{1-3}$ alkyl, C$_{13}$ alkoxy, halo, cyano, dimethylamino, CF$_3$, C$_2$F$_5$, OCF$_3$, SO$_2$Me or acetyl.

"Aryl" denotes either the 6-carbon benzene ring or the condensed 6-carbon rings of other aromatic derivatives (see, e.g., *Hawley's Condensed Chemical Dictionary* (13 ed.), R. J. Lewis, ed., J. Wiley & Sons, Inc., New York (1997)); aryl includes, without limitation, phenyl, napthyl, indanyl and indenyl. "Heteroaryl" rings are aryl rings in which one or more, typically from 1–4, of the ring-member carbon atoms is replace by an atom other than a carbon atom, i.e., a heteroatom (typically O, N or S). Heteroaryl includes, without limitation: pyridyl, pyrimidinyl, pyrazinyl, triazolyl, tetrazolyl, indazolyl, thienyl, isoxazolyl, 2,3-dihydrobenzofuranyl, 2,3-dihydrobenzsothienyl, 2,3-dihydrobenzothienyl-S-oxide, indolinyl, benzoxazolin-2-on-yl and benzodioxolanyl. "Alkyl" means saturated hydrocarbon chains, branched or unbranched, having the specified number of carbon atoms. "Alkenyl" means hydrocarbon chains of either a straight or branched configuration and one or more unsaturated carbon-carbon bonds, which may occur in any stable point along the chain, such as ethenyl, propenyl, and the like. "Alkynyl" means hydrocarbon chains of either a straight or branched configuration and one or more triple carbon-carbon bonds, which may occur in any stable point along the chain, such as ethynyl, propynyl and the like. "Alkoxy" means an alkyl group of indicated number of carbon atoms attached through an oxygen bridge. "Cycloalkyl" means saturated ring groups, including mono-, bi- or polycyclic ring systems, such as cyclopropyl, cyclobutyl, cyclopentyl, cyclohexyl, and so forth. "Halo" or "halogen" means fluoro, chloro, bromo, and iodo. "Haloalkyl" means both branched and straight-chain alkyls having the specified number of carbon atoms, substituted with 1 or more halogens. "Haloalkoxy" means an alkoxy group substituted by at least one halogen atom. "Substituted" means that one or more hydrogen on the designated atom is replaced with a selection from the indicated group, provided that the designated atom's normal valency is not exceeded, and that the substitution results in a stable compound. "Unsubstituted" atoms bear all of the hydrogen atoms dictated by their valency. When a substituent is keto, then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

Preferably, R$^1$ is —C(R$^8$)(R$^9$)—O—R$^{10}$. More preferably, presently, R$^8$ is H, R$^9$ is C$_2$H$_5$ or C$_3$H$_7$ and R$^{10}$ is C$_2$H$_5$. Preferably, R$^2$ is unsubstituted C$_{1-4}$ alkyl; more preferably, presently, $R^2$ is $C_2H_5$. $R^3$ and $R^4$ are preferably each H. X is preferably a single bond.

D is preferably phenyl, more preferably a phenyl group of the formula:

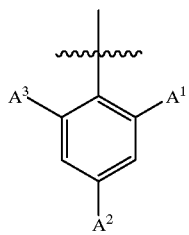

wherein each of $A^1$, $A^2$ and $A^3$ is selected from the group consisting of H, $C_{1-6}$ alkyl, $C_{1-6}$ alkoxy, halogen and $C_{1-4}$ haloalkyl. Even more preferably: $A^1$ is H, $CH_3$ or Cl; $A^2$ is Cl, $-OCH_3$ or $-OCHF_2$; and, $A^3$ is H or $CH_3$. Most preferably, presently, $A^1$ is Cl and $A^3$ is H.

Each of $R^1-R^{12}$, X, D and $A^1-A^5$ are any of the possible members of the groups listed hereinabove for these substituents. $R^2$, for example, being C1–4 alkyl or C3–8 cycloalkyl is each and every one of the members of these groups, i.e., is C1, C2, C3 and C4 alkyl, as well as C3, C4, C5, C6, C7 and C8 cycloalkyl. Moreover, selection of a substituent as a specific member of one of its groups does not limit the choice of the other substituents to less than all of the available selections.

$R^1$ is preferably $-CR^8R^9R^{10}$, and each of $R^8$, $R^9$ and $R^{10}$ is preferably H, C1, C2, C3 or C4 alkyl. Moreover, each of the substituents is any one of these five possibilities independently of the identity of the other substituents. Thus, there are at least 125 groups of preferred compounds, each of which is characterized by a different, but preferred, combination of $R^8$, $R^9$ and $R^{10}$ in $R^1$. These groups of compounds are listed in Tables A and B (hereinbelow).

TABLE A

| | $R^8$ Alkyl | | | | |
|---|---|---|---|---|---|
| $R^9$ | H | C1 | C2 | C3 | C4 |
| H | A1 | A2 | A3 | A4 | A5 |
| C1 Alkyl | A6 | A7 | A8 | A9 | A10 |
| C2 Alkyl | A11 | A12 | A13 | A14 | A15 |
| C3 Alkyl | A16 | A17 | A18 | A19 | A20 |
| C4 Alkyl | A21 | A22 | A23 | A24 | A25 |

TABLE B

| | $R^{10}$ Alkyl | | | | |
|---|---|---|---|---|---|
| $R^8 + R^9$ | H | C1 | C2 | C3 | C4 |
| X1 | B1 | B2 | B3 | B4 | B5 |
| X2 | B6 | B7 | B8 | B9 | B10 |
| X3 | B11 | B12 | B13 | B14 | B15 |
| X4 | B16 | B17 | B18 | B19 | B20 |
| X5 | B21 | B22 | B23 | B24 | B25 |
| X6 | B26 | B27 | B28 | B29 | B30 |
| X7 | B31 | B32 | B33 | B34 | B35 |
| X8 | B36 | B37 | B38 | B39 | B40 |
| X9 | B41 | B42 | B43 | B44 | B45 |
| X10 | B46 | B47 | B48 | B49 | B50 |
| X11 | B51 | B51 | B53 | B54 | B55 |
| X12 | B56 | B57 | B58 | B59 | B60 |
| X13 | B61 | B62 | B63 | B64 | B65 |
| X14 | B66 | B67 | B68 | B69 | B70 |
| X15 | B71 | B72 | B73 | B74 | B75 |

TABLE B-continued

| | $R^{10}$ Alkyl | | | | |
|---|---|---|---|---|---|
| $R^8 + R^9$ | H | C1 | C2 | C3 | C4 |
| X16 | B76 | B77 | B78 | B79 | B80 |
| X17 | B81 | B82 | B83 | B84 | B85 |
| X18 | B86 | B8 | B88 | B89 | B90 |
| X19 | B91 | B92 | B93 | B94 | B95 |
| X20 | B96 | B97 | B98 | B99 | B100 |
| X21 | B101 | B102 | B103 | B104 | B105 |
| X22 | B106 | B107 | B108 | B109 | B110 |
| X23 | B111 | B112 | B113 | B114 | B115 |
| X24 | B116 | B117 | B118 | B119 | B120 |
| X25 | B121 | B122 | B123 | B124 | B125 |

Table A specifies the identity of the substituent "$R^8$" in preferred compounds provided herein; these are listed, in the top row from left to right, as H, and then C1, C2, C3 and C4 alkyl. The identity of the substituent "$R^9$" in preferred compounds is also given, along the left side, from top to bottom, as H, and then C1, C2, C3 and C4 alkyl. Thus, each cell of the table identifies a specific combination of $R^8$ and $R^9$ in a preferred compound. Thus, each cell of the table identifies a specific combination of $R^8$ and $R^9$ in a preferred compound. Each cell is itself identified by an alphanumeric combination specifying the cell's location within the table.

Table B specifies the identity of the substituent "$R^{10}$" in preferred compounds provided hererein; these are listed, in the top row from left to right, as H, and then C1, C2, C3 and C4 alkyl. Moreover, the R8/R9 combinations set forth in in Table 1 are listed along the left side of the table, from top to bottom, in terms of their cell number from Table A (e.g., "X1" refers to that set of compounds wherein $R^8$ and $R^9$ are each H). Each cell of Table B thus specifies a specific combination of $R^8$, $R^9$ and $R^{10}$ (e.g., "B1" refers to that set of compounds wherein each of $R^8$, $R^9$ and $R^{10}$ are H).

$R^2$ is preferably C1, C2, C3 or C4 alkyl (each being unsubstituted). Table C hereinbelow lists the combinations of each of these with each of the $R^8/R^9/R^{10}$ combinations from Table B:

TABLE C

| | $R^1$ ALKYL | | | |
|---|---|---|---|---|
| $R^8/R^9/R^{10}$ | C1 | C2 | C3 | C4 |
| B1 | C1 | C2 | C3 | C4 |
| B2 | C5 | C6 | C7 | C8 |
| B3 | C9 | C10 | C11 | C12 |
| B4 | C13 | C14 | C15 | C16 |
| B5 | C17 | C18 | C19 | C20 |
| B6 | C21 | C22 | C23 | C24 |
| B7 | C25 | C26 | C27 | C28 |
| B8 | C29 | C30 | C31 | C32 |
| B9 | C33 | C34 | C35 | C36 |
| B10 | C37 | C38 | C39 | C40 |
| B11 | C41 | C42 | C43 | C44 |
| B12 | C45 | C46 | C47 | C48 |
| B13 | C49 | C50 | C51 | C52 |
| B14 | C53 | C54 | C55 | C56 |
| B15 | C57 | C58 | C59 | C60 |
| B16 | C61 | C62 | C63 | C64 |
| B17 | C65 | C66 | C67 | C68 |
| B18 | C69 | C70 | C71 | C72 |
| B19 | C73 | C74 | C75 | C76 |
| B20 | C77 | C78 | C79 | C80 |
| B21 | C81 | C82 | C83 | C84 |
| B22 | C85 | C86 | C87 | C88 |
| B23 | C89 | C90 | C91 | C92 |
| B24 | C93 | C94 | C95 | C96 |
| B25 | C97 | C98 | C99 | C100 |
| B26 | C101 | C102 | C103 | C104 |

TABLE C-continued

| $R^8/R^9/R^{10}$ | \multicolumn{4}{c}{$R^1$ ALKYL} |
| --- | --- | --- | --- | --- |
|  | C1 | C2 | C3 | C4 |
| B27 | C105 | C106 | C107 | C108 |
| B28 | C109 | C110 | C111 | C112 |
| B29 | C113 | C114 | C115 | C116 |
| B30 | C117 | C118 | C119 | C120 |
| B31 | C121 | C122 | C123 | C124 |
| B32 | C125 | C126 | C127 | C128 |
| B33 | C129 | C130 | C131 | C132 |
| B33 | C133 | C134 | C135 | C136 |
| B34 | C137 | C138 | C139 | C140 |
| B35 | C141 | C142 | C143 | C144 |
| B36 | C145 | C146 | C147 | C148 |
| B37 | C149 | C150 | C151 | C152 |
| B38 | C153 | C154 | C155 | C156 |
| B39 | C157 | C158 | C159 | C160 |
| B40 | C161 | C162 | C163 | C164 |
| B41 | C165 | C166 | C167 | C168 |
| B42 | C169 | C170 | C171 | C172 |
| B43 | C173 | C174 | C175 | C176 |
| B44 | C177 | C178 | C179 | C180 |
| B45 | C181 | C182 | C183 | C184 |
| B46 | C185 | C186 | C187 | C188 |
| B47 | C189 | C190 | C191 | C192 |
| B48 | C193 | C194 | C195 | C196 |
| B49 | C197 | C198 | C199 | C200 |
| B50 | C201 | C202 | C203 | C204 |
| B51 | C205 | C206 | C207 | C208 |
| B52 | C209 | C210 | C211 | C212 |
| B53 | C213 | C214 | C215 | C216 |
| B54 | C217 | C218 | C2190 | C220 |
| B55 | C221 | C222 | C223 | C224 |
| B56 | C225 | C226 | C227 | C228 |
| B57 | C229 | C230 | C231 | C232 |
| B58 | C233 | C234 | C235 | C236 |
| B59 | C237 | C238 | C239 | C240 |
| B60 | C241 | C242 | C243 | C244 |
| B61 | C245 | C246 | C2247 | C248 |
| B62 | C249 | C250 | C251 | C252 |
| B63 | C253 | C254 | C255 | C256 |
| B64 | C257 | C258 | C259 | C260 |
| B65 | C261 | C262 | C263 | C264 |
| B66 | C265 | C266 | C267 | C268 |
| B67 | C269 | C270 | C271 | C272 |
| B68 | C273 | C274 | C275 | C276 |
| B69 | C277 | C278 | C279 | C280 |
| B70 | C281 | C282 | C283 | C284 |
| B71 | C285 | C286 | C287 | C288 |
| B72 | C289 | C290 | C291 | C292 |
| B73 | C293 | C294 | C295 | C296 |
| B74 | C297 | C298 | C299 | C300 |
| B75 | C301 | C302 | C303 | C304 |
| B76 | C305 | C306 | C307 | C308 |
| B77 | C309 | C310 | C311 | C312 |
| B78 | C313 | C314 | C315 | C316 |
| B79 | C317 | C318 | C319 | C320 |
| B80 | C321 | C322 | C323 | C324 |
| B81 | C325 | C326 | C327 | C328 |
| B82 | C329 | C330 | C331 | C332 |
| B83 | C333 | C334 | C335 | C336 |
| B84 | C337 | C338 | C339 | C340 |
| B85 | C341 | C342 | C343 | C344 |
| B86 | C345 | C346 | C347 | C348 |
| B87 | C349 | C350 | C351 | C352 |
| B88 | C353 | C354 | C355 | C356 |
| B89 | C357 | C358 | C359 | C360 |
| B90 | C361 | C362 | C363 | C364 |
| B91 | C365 | C366 | C367 | C368 |
| B92 | C369 | C370 | C371 | C372 |
| B93 | C373 | C374 | C375 | C376 |
| B94 | C377 | C378 | C379 | C380 |
| B95 | C381 | C383 | C383 | C384 |
| B96 | C385 | C386 | C387 | C388 |
| B97 | C389 | C390 | C391 | C392 |
| B98 | C393 | C394 | C395 | C396 |
| B99 | C397 | C398 | C399 | C400 |
| B100 | C401 | C402 | C403 | C404 |
| B101 | C405 | C406 | C407 | C408 |
| B102 | C409 | C410 | C411 | C412 |
| B103 | C413 | C414 | C415 | C416 |
| B104 | C417 | C418 | C419 | C420 |
| B105 | C421 | C422 | C423 | C424 |
| B106 | C425 | C426 | C427 | C428 |
| B107 | C429 | C430 | C431 | C432 |
| B108 | C433 | C434 | C435 | C436 |
| B109 | C437 | C438 | C439 | C440 |
| B110 | C441 | C442 | C443 | C444 |
| B111 | C445 | C446 | C447 | C448 |
| B112 | C449 | C450 | C451 | C452 |
| B113 | C453 | 454 | C455 | C456 |
| B114 | C457 | C458 | C459 | C460 |
| B115 | C461 | C462 | C463 | C464 |
| B116 | C465 | C466 | C467 | C468 |
| B117 | C469 | C470 | C471 | C472 |
| B118 | C473 | C474 | C475 | C476 |
| B119 | C477 | C478 | C479 | C480 |
| B120 | C481 | C482 | C483 | C484 |
| B121 | C485 | C486 | C487 | C488 |
| B122 | C489 | C490 | C491 | C492 |
| B123 | C493 | C494 | C495 | C496 |
| B124 | C497 | C498 | C499 | C500 |
| B125 | C501 | C502 | C503 | C504 |

Also as described hereinabove, D is most preferably a phenyl substituted with $A^1$ (presently preferably H or $CH_3$), $A^2$ (preferably Cl, $-OCH_3$ or $-OCHF_2$) and $A^3$ (H or $CH_3$). Tables D and DD hereinbelow identify individual sets of compounds containing each of the possible specific combinations of these groupings. Table D lists combinations of $A^1$ and $A^3$ (e.g., cell "D1" represents that set of compounds wherein $A^1$ and $A^3$ are each H); Table DD lists combinations of $A^1/A^3$ with the various presently preferred members of $A^2$ (e.g., cell "DD1" represents that set of compounds wherein $A^2$ is Cl and the $A^1/A^3$ combination is represented by cell "D1" (i.e., $A^1$ and $A^3$ are each H)):

TABLE D

|  | \multicolumn{2}{c}{A} |
| --- | --- | --- |
| $A^1$ | H | $CH_3$ |
| H | D1 | D2 |
| $CH_3$ | D3 | D4 |

TABLE DD

|  | \multicolumn{3}{c}{$A^2$} |
| --- | --- | --- | --- |
| $A^1/A^2$ | Cl | $-OCH_3$ | $-OCHF_2$ |
| D1 | DD1 | DD2 | DD3 |
| D2 | DD4 | DD5 | DD6 |
| D3 | DD7 | DD8 | DD9 |
| D4 | DD10 | DD11 | DD12 |

Furthermore, as described hereinabove, this invention provides presently preferred compounds comprising combinations of any of the preferred members of $R^1$ and $R^2$ (identified in Table C hereinabove with the designations "C1–C500") with any of the specific $A^1/A^2/A^3$ combinations listed in Table DD; these $R^1*R^2/A^1*A^2*A^3$ combinations, and hence, individual preferred compounds are listed specifically in Table E hereinbelow. Across the top row of the table, from left to right, are listed individual sets of compounds comprising combinations of the various specific, individual $A^1$, $A^2$ and $A^3$ substituents of the phenyl ring D, as identified by their corresponding cell number in Table DD. The leftmost column of the table lists individual sets of compounds comprising the various specific, individual $R^1$ and $R^2$ substituents, as identified by their corresponding cell number in table C. In this regard, cell number C1 (and hence, compounds in which $R^1$ is C1 alkyl, $R^2$ is —$CR^8R^9OCR^{10}$, and $R^8$, $R^9$ and $R^{10}$ are each H) corresponds to the individual compounds listed in Table E as E1, E501, E1001, E1501, E2001, E2501, E3001, E3501, E4001, E4501, E5001 and E5501; the other cells of Table C (C2–C500) have a similar correspondence to the individual compounds listed in Table E.

In addition to the compounds described and listed hereinabove, this invention provides their corresponding pharmaceutically acceptable salt, radiolabelled, various stereoisomeric and prodrug forms. "Pharmaceutically acceptable salts" of compounds of this invention are also provided herein. The phrase "pharmaceutically acceptable" is employed to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids.

Pharmaceutically acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Pharmaceutically acceptable salt forms of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Radiolabelled compounds, i.e. wherein one or more of the atoms described are replaced by a radioactive isotope of that atom (e.g. C replaced by $^{14}C$ or by $^{11}C$, and H replaced by $^3H$ or $^{18}F$), are also provided for herein. Such compounds have a variety of potential uses, e.g. as standards and reagents in determining the ability of a potential pharmaceutical to bind to neurotransmitter proteins, or for imaging compounds of this invention bound to biological receptors in vivo or in vitro.

Each of the stereoisomeric forms of this invention's compounds is also provided for herein. That is, the compounds can have one or more asymmetric centers or planes, and all chiral (enantiomeric and diastereomeric) and racemic forms of the compounds are included in the present invention. Many geometric isomers of olefins, C=N double bonds, and the like can also be present in the compounds, and all such stable isomers are contemplated in the present invention. Compounds are isolated in either the racemic form, or in the optically pure form, for example, by chiral chromatography or chemical resolution of the racemic form.

Prodrug forms of this invention's compounds are also provided for herein. Such "prodrugs" are compounds comprising this invention's compounds and moieties covalently bound to the parent compounds such that the portions of the parent compound most likely to be involved with toxicities in subjects to which the prodrugs have been administered are blocked from inducing such effects. However, the prodrugs are also cleaved in the subjects in such a way as to release the parent compound without unduly lessening its therapeutic potential. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, and benzoate derivatives of alcohol, and amine functional groups in the compounds of Formulae (I–III).

The compounds provided herein are, for example and without limitation, made by the synthetic routes and schemes set forth hereinbelow.

Synthesis

Imidazo[1,2-a]pyrazines (1) of the present invention may be prepared from intermediate compounds of Formula (2) using the procedures outlined in Scheme 1.

Scheme 1

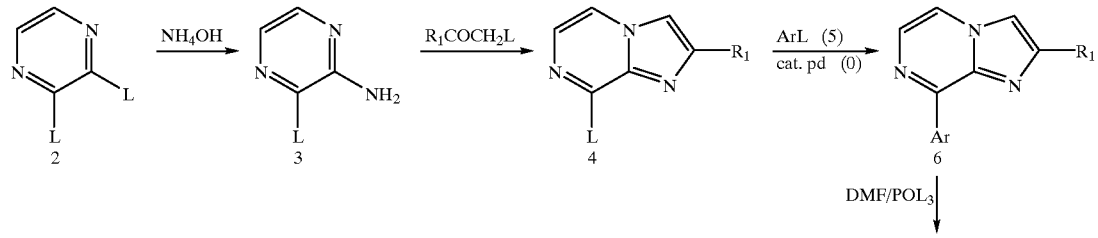

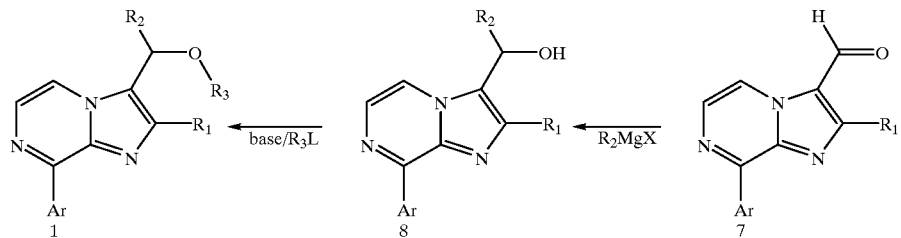

Compounds of Formula (2) (where L=leaving groups such as halogen) may be treated with ammonia or aqueous ammonia in the presence or absence an inert solvent such as alkyl alcohols, at reaction temperatures ranging from −80° C. to 250° C. to give products of Formula (3) (where L is halogen). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methyl-pyrrolidin-2-one), dialkylsulfoxides (preferably dimethylsulfoxide), aromatic hydrocarbons (preferably benzene or toluene), alkyl esters (preferably EtOAc) or haloalkanes of 1 to 10 carbons and 1 to 10 halogens (preferably dichloromethane).

The resulting intermediates (3) may then be reacted with alpha haloketone derivatives in a solvent such as aliphatic alcohols or an inert solvent at temperatures ranging from −20° C. to 150° C. to give compounds of Formula (4). Inert solvents may include, but are not limited to, polyethers (preferably 1,2-dimethoxyethane), dialkyl ethers (preferably diethyl ether), cyclic ethers (preferably tetrahydrofuran or 1,4-dioxane) or aromatic hydrocarbons (preferably benzene or toluene).

The compounds of Formula (4) may be coupled to an aromatic compound of Formula (5) to give a compound of Formula (6), with elimination of the leaving group (L). For compound (4), L represents a halide, psuedohalide (such as mesylate, tosylate or triflate), or thiomethyl. For compound (5), L represents groups such as lithium, bromomagnesium, chlorozinc, (dihydroxy)boron, (dialkoxy)boron, trialkylstannyl and the like. The coupling reaction may be performed in the presence of an appropriate catalyst, such as tetrakis(triphenylphosphine)palladium, bis(triphenylphosphine)palladium dichloride, [1,3-bis(diphenylphosphino)propane]nickel dichloride, etc. Two particularly useful methods involve the coupling of chloro-heterocycles with in-situ-prepared arylzinc reagents according to the method of Negishi et al. (*J. Org. Chem.* 1977, 42, 1821), and the coupling with arylboronic esters according to the method of Suzuki et al. (*Chem. Letters* 1989, 1405). Appropriate solvents for reactions of this type usually include tetrahydrofuran, diethyl ether, dimethoxyethane, dimethylformamide, or dimethylsulfoxide. Typical temperatures range from ambient up to the boiling point of the solvent.

The compound of Formula (6) may be converted to a compound of Formula (7) by treatment with phosphorous oxyhalide in dialkylformamide. Compounds of Formula (8) may be obtained from a compound of Formula (7) by treatment with alkyllithiums, alkylmagnesiumhalides, alkyllithiumcuprates or alkylzinc reagents in an inert solvent such as tetrahydrofuran, diakylether or aromatic hydrocarbons.

The compound of Formula (8) can be converted to a compound of invention (1) by alkylating the alcohol with alkyl halides in the presence of base in an inert solvent. Bases may include, but are not limited to, alkali metal hydrides (preferably sodium hydride). Inert solvents include, but are not limited to, dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from −20° C. to 100° C.

Alternatively, imidazo[1,2-a]pyrazine (1) of the present invention may be obtained by following the steps outlined in Scheme 2. A compound of Formula (4) may be converted to a compound of Formula (9) by following similar conditions for the conversion of compounds of Formula (6) to (7) outlined in Scheme 1. A compound of Formula (10) may be obtained from compound (9) by following conditions for the conversion of Formula (7) to (8) as shown in Scheme 1. Compound (10) may be alkylated to compound (11) by similar conditions outlined for Formula (8) to (1) outlined in scheme 1. Finally a compound of Formula (11) can be converted to a compound of invention (1) using the conditions for the conversion of Formula (4) to (6).

Scheme 2

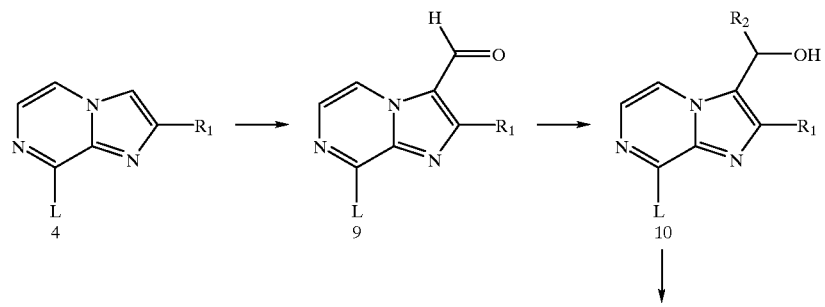

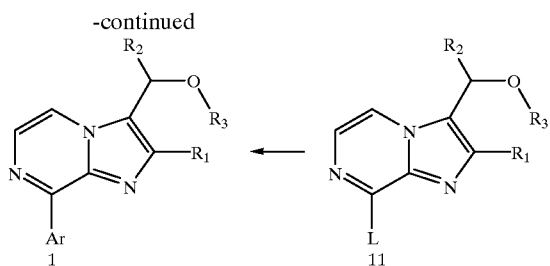

Alternatively, imidazo[1,2-a]pyrazines of the present invention may be obtained by following the steps outlined in Scheme 3. The compound of Formula (7) may be oxidized to a compound of Formula (12) by following well known methods outlined in literature (see: Comprehensive Organic Transformations by R. C. Larock, 1989, pp 604–614).

Scheme 3

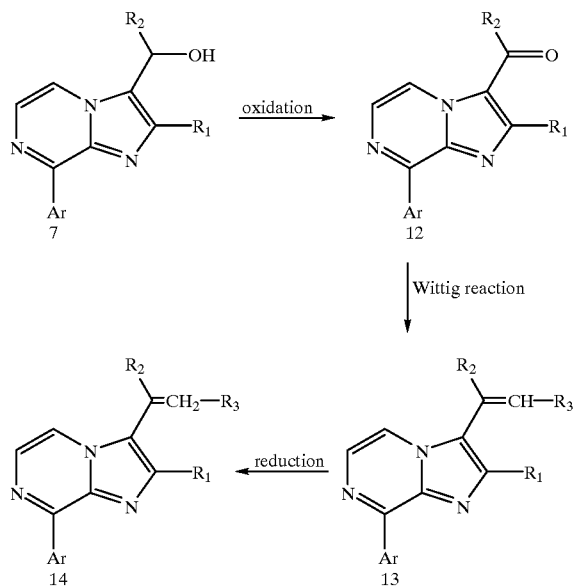

The compound of Formula (12) may be subjected to Wittig or Tebbe's reaction conditions to afford a compound of Formula (13) which may be reduced to a compound of Formula (14).

The nitrogen containing side chain analogs of imidazo[1,2-a]pyrazine derivatives can be synthesized by following procedures outlined in Scheme 4.

Scheme 4

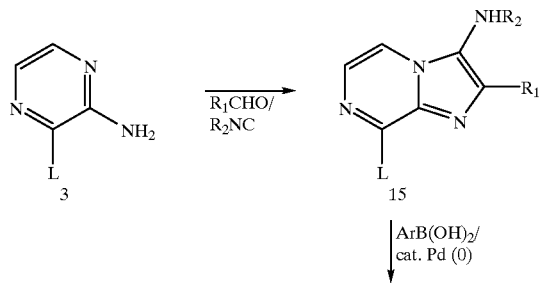

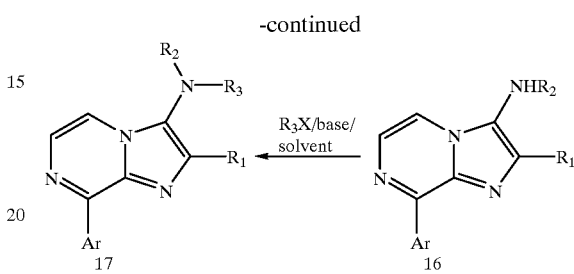

The compound of the Formula (3) may be converted to a 3-aminoimidazo[1,2-a]pyrazine derivative of Formula (15) by a three component condensation reaction consisting of primary amine, aldehyde and isonitriles in the presence of an acid in an inert solvent. Acids may include, but are not limited to alkanoic acids of 2 to 10 carbons (preferably acetic acid), haloalkanoic acids (2–10 carbons, 1–10 halogens, such as trifluoroacetic acid), alkanesulfonic acids of 1 to 10 carbons (preferably methanesulfonic acid), hydrochloric acid. Also acids include Lewis acids but not limited to aluminum halides, borontrifluoride etherates, $LiBF_4$, Magnesium halides, tin halides, titanium halides, titanium alkoxides, zinc halides and scandium triflates. Inert solvents may include, but are not limited to, polyethers (preferably 1,2-dimethoxyethane), dialkyl ethers (preferably diethyl ether), cyclic ethers (preferably tetrahydrofuran or 1,4-dioxane), haloalkanes or aromatic hydrocarbons (preferably benzene or toluene). The compound of Formula (15) may be converted to the compound of Formula (17) by following similar conditions outlined in Scheme 1.

Moreover, in addition to compounds made by these routes and schemes, this invention provides pharmaceutical compositions comprising pharmaceutically acceptable carriers and therapeutically effective amounts of the compounds. "Pharmaceutically acceptable carriers" are media generally accepted in the art for the delivery of biologically active agents to animals, in particular, mammals. Such media are formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted.

Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's*

*Pharmaceutical Sciences,* 17th ed., Mack Publishing Company, Easton, Pa., 1985, the contents of which are incorporated herein by reference.

Compounds provided herein are antagonists of receptors for corticotropin releasing factor ("CRF"), a 41 amino acid peptide that is the primary physiological regulator of pro-opiomelanocortin (POMC)-derived peptide secretion from the anterior pituitary gland [J. Rivier et al., *Proc. Nat. Acad. Sci. (USA)* 80:4851 (1983); W. Vale et al., *Science* 213:1394 (1981)]. Immunohistochemical localization of CRF has also demonstrated that CRF has a broad extrahypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

CRF concentrations have been found to be significantly increased in the cerebral spinal fluid (CSF) of drug-free individuals afflicted with affective disorder or depression [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. Moreover, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)].

CRF produces anxiogenic effects in animals. Moreover, interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist alpha-helical ovine CRF (9-41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)]. The contents of the above-cited documents are incorporated herein by reference.

Thus, compounds provided herein which, because of their antagonism of CRF receptors, alleviate the effects of CRF overexpression are expected to be useful in treating these and other disorders. Such treatable disorders include, for example and without limitation: affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis and hypoglycemia.

This invention thus further provides a method of treating a subject afflicted with a disorder characterized by CRF overexpression, such as those described hereinabove, which comprises administering to the subject a pharmaceutical composition provided herein. Such compositions generally comprise a therapeutically effective amount of a compound provided herein, that is, an amount effective to ameliorate, lessen or inhibit disorders characterized by CRF overexpression. Such amounts typically comprise from about 0.1 to about 1000 mg of the compound per kg of body weight of the subject to which the composition is administered. Therapeutically effective amounts can be administered according to any dosing regimen satisfactory to those of ordinary skill in the art.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as but not limited to lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

This invention is described in the following examples, which those of ordinary skill in the art will readily understand are not limiting on the invention as defined in the claims which follow thereafter.

EXAMPLES

Table 1 is a brief summary of compounds provided herein, made according to the synthetic schemes described hereinabove and the examples provided hereinbelow.

Analytical data were recorded for the compounds described below using the following general procedures. Proton NMR spectra were recorded on an Varian FT-NMR (300 MHz); chemical shifts were recorded in ppm (δ) from an internal tetramethysilane standard in deuterochloroform or deuterodimethylsulfoxide as specified below. Mass spectra (MS) or high resolution mass spectra (HRMS) were recorded on a Finnegan MAT 8230 spectrometer (using chemical ionization (CI) with $NH_3$ as the carrier gas or gas chromatography (GC) as specified below) or a Hewlett Packard 5988A model spectrometer. Melting points were recorded on a Buchi Model 510 melting point apparatus and are uncorrected. Boiling points are uncorrected. All pH determinations during workup were made with indicator paper.

Reagents were purchased from commercial sources and, where necessary, purified prior to use according to the general procedures outlined by D. Perrin and W. L. F. Armarego, *Purification of Laboratory Chemicals,* 3rd ed., (New York: Pergamon Press, 1988). Chromatography (thin layer (TLC) or preparative) was performed on silica gel using the solvent systems indicated below. For mixed solvent systems, the volume ratios are given. Otherwise, parts and percentages are by weight.

TABLE 1

| Ex. | X | Y | Z | $R_1$ | $R_2$ | mp (° C.) |
|---|---|---|---|---|---|---|
| 1 | Cl | Cl | H | Et | CH(Me)OH | amorph |
| 2 | Cl | Cl | H | Et | CH(Me)OMe | oil |
| 3 | Cl | Cl | H | Et | CH(Me)OEt | oil |
| 4 | Cl | Cl | H | Et | CH(Et)OH | 70–71 |
| 5 | Cl | Cl | H | Et | CH(Et)OMe | oil |
| 6 | Cl | Cl | H | Et | CH(Et)OEt | oil |
| 7 | Cl | Cl | H | Et | CH(n-$C_3H_7$)OH | 159–160 |
| 8 | Cl | Cl | H | Et | CH(n-$C_3H_7$)OMe | oil |
| 9 | Cl | Cl | H | Et | CH(n-$C_3H_7$)OEt | 65–67 |
| 10 | Cl | Cl | H | Et | CH(C≡CMe)OH | 81–82 |
| 11 | Cl | Cl | H | Et | CH(C≡CMe)OMe | oil |
| 12 | Cl | Cl | H | Et | CH(C≡CMe)OEt | oil |
| 13 | Cl | Cl | H | Et | CH(CPM)OH | 131–132 |
| 14 | Cl | Cl | H | Et | CH(CPM)OEt | oil |
| 15 | Cl | Cl | H | Et | CH(allyl)OEt | oil |
| 16 | Cl | Cl | H | Et | CH(n-Bu)OH | oil |
| 17 | Cl | Cl | H | Et | CH(n-Bu)OEt | oil |
| 18 | Cl | Cl | H | Et | CH[CH(Me)Et]OH | amorph. |
| 19 | Cl | Cl | H | Et | CH[CH(Me)Et]OEt | oil |
| 20 | Cl | Cl | H | Me | CH(n-$C_3H_7$)OH | amorph. |
| 21 | Cl | Cl | H | Me | CH(n-$C_3H_7$)Oet | 110–111 |
| 22 | Cl | OMe | H | Et | CH(Et)OH | 145–146 |
| 23 | Cl | OMe | H | Et | CH(Et)Oet | oil |
| 24 | Cl | OMe | H | Et | CH(n-$C_3H_7$)OH | 152–153 |
| 25 | Cl | OMe | H | Et | CH(n-$C_3H_7$)OEt | oil |
| 26 | Cl | $OCHF_2$ | H | Et | CH(Et)OH | 144–145 |
| 27 | Cl | $OCHF_2$ | H | Et | CH(Et)$OC_2H_5$ | oil |
| 28 | Cl | $OCHF_2$ | H | Et | CH(n-$C_3H_7$)OH | 123–124 |
| 29 | Cl | $OCHF_2$ | H | Et | CH(n-$C_3H_7$)OEt | 67–68 |
| 30 | Me | $OCHF_2$ | Me | Et | CH(n-$C_3H_7$)OEt | 83–84 |
| 31 | Me | $OCHF_2$ | H | Et | CH(n-$C_3H_7$)OH | 147–148 |
| 32 | Me | $OCHF_2$ | H | Et | CH(n-$C_3H_7$)OEt | oil |
| 33 | Cl | Cl | H | Et | C(=O)-n-$C_3H_7$ | 95–96 |
| 34 | Cl | Cl | H | Et | C(=$CH_2$)-n-$C_3H_7$ | oil |

TABLE 1-continued

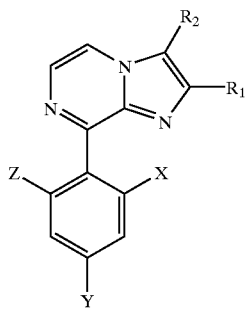

| Ex. | X | Y | Z | $R_1$ | $R_2$ | mp (° C.) |
|---|---|---|---|---|---|---|
| 35 | H | Cl | H | Et | N(Bz)-n-$C_3H_7$ | oil |
| 36 | Cl | Cl | H | Et | N(Bz)-n-$C_3H_7$ | oil |
| 37 | Cl | Cl | H | Et | NH(Bz) | oil |
| 38 | Cl | Cl | H | Et | N(Bz)Et | oil |
| 39 | Cl | Cl | H | Et | N(Et)-n-Bu | oil |
| 40 | Cl | Cl | H | Et | N(allyl)Et | oil |

Example 1

8-(2,4-dichlorophenyl)-2-ethyl-3-(1-hyroxyethyl) imidazo [1,2-a]pyrazine

Part A: Synthesis of 3-amino-2-chloropyrazine: (Ref: S. Okada et al Chem. Pharm. Bull. 1971, 19(7), 1344–1357). A mixture of 2,3-dichloropyrazine (20 g, 0.134 moles) and 28% aq. $NH_4OH$ (120 mL) was heated in a resealable pressure tube at 140° C. for 24 h. The solution was cooled and filtered and the off-white crystals separated and dried to afford 16.6 g material (96%, mp 165–166° C.). The crude was quite pure by NMR and used in the next step without purification.

Part B: Synthesis of 8-chloro-2-ethylimidazo[1,2-a] pyrazine: To a solution of 2-amino-3-chloropyrazine (19.5 g, fw=129, 0.15 moles) in dioxane (250.0 mL) was treated with 90% 1-bromo-2-butanone (25 g, fw=151, 1.1 moles, Aldrich) and stirred under nitrogen for 4 h followed by reflux for 48 h. Brick red colored solid separated from the mixture. TLC (1:50 MeOH/$CH_2Cl_2$) showed a new spot at Rf=0.30 along with disappearance of starting material spot at Rf=0.42. The reaction mixture was cooled to room temperature filtered the solid and washed the solid with diethyl ether (2×100 mL). NMR of the salt in DMSO-D6 revealed a clean product. The salt was dissolved in water (500 mL), adjusted the pH to 8 using solid $Na_2CO_3$, extracted with EtOAc, washed with brine, dried ($MgSO_4$) and concentrated in vacuum to afford pale yellow solid. The crude (20 g, 74% yield, mp 73–74° C.) was found to be quite pure by NMR and used without purification in the next step.

Part C: Synthesis of 8-(2,4-dichlorophenyl)-2-ethylimidazo[1,2-a]pyrazine: A mixture of 8-chloro-2-ethylimidazo[1,2-a]pyrazine (9.05 g, 0.05 mol, fw=181) and 2,4-dichlorobenzeneboronic acid (10.5 g, 0.055 mol, fw=190.81) in toluene (200.0 mL) was treated with 2M aq. $Na_2CO_3$ (40.0 mL) and EtOH (20.0 mL). The reaction mixture was degassed under vacuum and purged with nitrogen (repeated 3 times) and then added $Pd(PPh_3)_2Cl_2$ (740 mg, 0.001 mol, fw=738.18, 2 mol %). After the addition the reaction mixture was degassed under vacuum and purged with nitrogen (repeated 3 times). The resultant mixture was refluxed under nitrogen for 24 h. TLC (1:50 MeOH/$CH_2Cl_2$) showed two new spots at Rf=0.53 and 0.35 along with trace amount of starting material spot at Rf=0.30. The reaction mixture was cooled to room temp and partitioned between 200 ml of 1:1 EtOAc/water. The aq. layer was extracted with EtOAc (2×150 mL), dried (MgSO$_4$) and concentrated in vacuum to afford yellow oil. The crude (15.1 g, brown yellow solid) was purified by flash column chromatography on a silica gel using 15% EtOAc/hexane to afford the top spot as pale yellow solid (760 mg, mp 71–72° C.)and characterized as 8-(4-chlorophenyl)-2-ethylimidazo[1,2-a] pyrazine. HRMS calcd. for $C_{14}H_{13}N_3Cl_1$: 258.0798. Found: 258.0788 (M+H). Further elution of the column with 30% EtOAc/hexane gave desired product (bottom spot) as white solid (8.6 g, 59% yield, 125–126° C.). HRMS calcd. for $C_{14}H_{12}N_3Cl_2$: 292.0408. Found: 292.0409 (M+H).

Part D: Synthesis of 8-(2,4-dichlorophenyl)-2-ethyl-3-formyl-imidazo[1,2-a]pyrazine: POCl$_3$ (99.6 g, 60.0 mL, 65.0 mmol, fw=153.33) was added dropwise to a cooled (0° C.) stirred solution of dry DMF (200 mL). The resultant mixture was stirred for additional 15 min. and then added 8-(2,4-dichlorophenyl)-2-ethylimidazo[1,2-a]pyrazine(14.6 g, 50.0 mmol, fw=292) to the reaction mixture. The reaction mixture was gradually brought to room temperature and stirred for 4 days. The reaction mixture appeared yellow in color. TLC (1:50 MeOH/CH$_2$Cl$_2$) revealed absence of starting material spot (Rf=0.35) and showed a new spot at Rf=0.4. The reaction mixture was quenched with ice (750 g), stirred the mixture for 30 min., neutralized with solid sodium carbonate and extracted with EtOAc (3×200 mL), dried (MgSO$_4$) and concentrated in vacuum to afford yellow solid. The solid was purified by flash column chromatography on a silica gel using 20% EtOAc/hexane to afford 11.7 g (73%, 93–94° C.) of white solid. Anal. calcd. for $C_{15}H_{11}Cl_2N_3O$: C, 56.27; H, 3.46; N, 13.12. Found: C, 56.13; H, 3.38; N, 12.96.

Part E: Synthesis of Title Compound: The aldehyde of Part D of Example 1 (0.320 g, 1.0 mmol) was dissolved in anhydrous THF (5.0 mL) and cooled to -78 C. under nitrogen. To this mixture was added dropwise 1.4 M MeMgBr in toluene/THF (3.0 mL, 4.2 mmol) and stirred at -78° C. for 3 h. TLC (1:10 MeOH/CH$_2$Cl$_2$) revealed absence of starting material spot (Rf=0.88) and showed a new spot at Rf=0.12. The reaction mixture was quenched with satd. NH$_4$Cl (10.0 mL), stirred the mixture for 10 min., extracted with EtOAc (3×25 mL), dried (MgSO$_4$) and concentrated in vacuum to afford yellow oil. The residue was purified by flash column chromatography on a silica gel using 2.5% MeOH/CH$_2$Cl$_2$ to afford 207 mg (62%) of amorphous wet white solid. HRMS calcd. for $C_{16}H_{16}Cl_2N_3O$: 336.0670. Found: 336.0678 (M+H).

Example 2

8-(2,4-dichlorophenyl)-2-ethyl-3-(1-methoxyethyl) imidazo[1,2-a]pyrazine

The alcohol from Part E of Example 1 (90.0 mg, 0.268 mmol) was dissolved in dry DMF (2.0 mL) under nitrogen. To this mixture was added 60% NaH (21.4 mg, 0.536 mmol, 2 equiv.)and stirred at room temperature for 30 mins. MeI (excess) was added to the mixture and stirred overnight. TLC (1:10 MeOH/CH$_2$Cl$_2$) revealed a new spot (Rf=0.31). The reaction mixture was quenched with water (5.0 mL), stirred the mixture for 10 mins., extracted with EtOAc (3×15 mL), dried (MgSO$_4$) and concentrated in vacuum to afford yellow oil. The residue was purified by flash column chromatography on a silica gel using 1% MeOH/CH$_2$Cl$_2$ to afford yellow oil (32 mg, 34% yield. HRMS calcd. for $C_{17}H_{18}Cl_2N_3O$: 350.0827. Found:350.0828 (M+H). The compounds of examples 3–32 shown in Table 1 were prepared by following the experimental conditions outlined in Examples 1 & 2, hereinabove.

Example 33

8-(2,4-dichlorophenyl)-2-ethyl-3-(1-oxo-butyl) imidazo[1,2-a]pyrazine

Part A: 8-(2,4-dichlorophenyl)-2-ethyl-3-(1-hydroxybutyl)imidazo[1,2-a]pyrazine: The aldehyde (1.6 g, 5.0 mmol, Part D of Example 1) was dissolved in anhydrous THF (25.0 mL) and cooled to -78° C. under nitrogen. To this mixture was added dropwise 2.0 M n-PrMgCl in diethyl ether (6.7 mL, 14.4 mmol) and stirred at -78° C. for 4 h. TLC (1:10 MeOH/CH$_2$Cl$_2$) revealed absence of starting material spot (Rf=0.88) and showed a new spot at Rf=0.05. The reaction mixture was quenched with saturated NH$_4$Cl (30.0 mL), stirred the mixture for 10 min., extracted with EtOAc (3×100 mL), dried (MgSO$_4$) and concentrated in vacuum to afford yellow oil. The residue was purified by flash column chromatography on a silica gel using 2.5% MeOH/CH$_2$Cl$_2$ to afford 1.63 g (84%, mp 159–160° C.) of desired product as white solid.

Part B: Title Compound: To a mixture of carbinol (1.1 g, 0.003 moles, fw364, Part A of Example 33) in toluene (25 mL) was added MnO$_2$ and refluxed under nitrogen for 24 h. TLC (1:10 MeOH/CH$_2$Cl$_2$) revealed absence of starting material spot (Rf=0.5) and showed a new spot at Rf=0.86. The reaction mixture was cooled to room temperature, filtered through celite, washed the celite with EtOAc (3×50 mL), and concentrated in vacuum to afford yellow oil. The residue was purified by flash column chromatography on a silica gel using 1% MeOH/CH$_2$Cl$_2$ to afford 580 mg (53%, mp 95–96° C.) of white solid.

Example 34

8-(2,4-dichlorophenyl)-2-ethyl-3-(1-propylvinyl) imidazo[1,2-a]pyrazine

To a solution of keto imidazopyrazine (181 mg, 0.5 mmol, Part B of Example 33) in THF (5.0 mL) at room temp was added 0.5 M toluene solution of the Tebbe reagent (1.2 mL, 0.6 mmol) dropwise under nitrogen atmosphere. The reaction mixture was slightly exothermic during addition and continued stirring for 1 h. TLC (3:7 EtOAc/hexane) revealed absence of starting material (Rf=0.5) along with a new spot (Rf=0.46). The reaction mixture was diluted with 15 mL of Et$_2$O and then added 3–5 drops of 1.0 N Aq. NaOH. After gas evolution ceases, the mixture was filtered through celite, evaporated to dryness and purified by flash column chromatography on a silica gel using 10% EtOAc/hexane to afford yellow oil (81 mg, 45%). HRMS calcd. for $C_{19}H_{20}N_3Cl_2$: 360.1034. Found:360.1033

The compound of example 35 was prepared according to the experimental conditions outlined in Examples 33 and 34, hereinabove Example 36

8-(2,4-dichlorophenyl)-2-ethyl-3-(N-propylbenzylamino)imidazo[1,2-a]pyrazine

Part A: 3-benzylamino-8-chloro-2-ethylimidazo[1,2-a] pyrazine: To a solution of 2-amino-3-chloropyrazine (1.3 g, fw=129, 10.0 mmole) in MeOH (50.0 mL) was treated with propionaldehyde (0.58 g, fw=58, 10.0 mmole, Aldrich), AcOH (1.2 g, 20 mmol, fw=60) and benzyl isocyanide (STENCH, 1.17 g, 10.0 mmol, fw=117.15, Aldrich). The resultant suspension was stirred at room temp overnight. TLC (1:50 MeOH/CH$_2$Cl$_2$) showed a new spot at Rf=0.24 along with unreacted starting material spot at Rf=0.42. The unreacted isocyanide was destroyed by acidifying the reaction mixture to pH 1 using 1N HCl. After acidification the reaction mixture was stirred at room temp for 30 mins, evaporated to dryness, residue dissolved in water, adjusted the pH to 8 using KHCO$_3$, extracted the reaction mixture with EtOAc (3×50 mL) and dried with anhydrous MgSO$_4$. The solvent was evaporated from the reaction mixture and the residue (pale yellow solid) was partitioned between 50 ml of 1:1 EtOAc/aq. NaHCO$_3$. The aq. layer was extracted with EtOAc (2×15 mL), dried (MgSO$_4$) and concentrated in vacuum to afford pale yellow solid (3.0 g). The crude was treated with CH$_2$Cl$_2$ and filtered the white solid (0.75 recovered starting material). The filtrate was evaporated and purified by flash column chromatography on a silica gel using 30% EtOAc/hexane to afford 0.42 g (34% yield) desired product as yellow oil.

Part B: N-Alkylation: A mixture of 3-benzyamino-8-chloro-2-ethylpyrazine (415 mg, 0.00145 moles, fw=286.45) in DMF (2.0 mL) was treated with 60% NaH (70 mg, 0.00174 moles, 1.2 equiv.) at room temp under nitrogen atmosphere and stirred for 15 mins. To this mixture was added 1-iodopropane (0.296 g, 0.00174 moles, 1.2 equiv.) and stirred at room temp for 4 h. TLC (1:50 MeOH/CH$_2$Cl$_2$) showed a new spot at Rf=0.33 along with several minor spots below the product. Since the starting material spot overlapped with one of the minor spots, the reaction was allowed to continue over weekend. The solvent from the reaction mixture was evaporated under vacuum, quenched with water, extracted with EtOAc (3×10 mL), dried with MgSO4. The solvent from the reaction mixture was evaporated and the crude was purified by flash column chromatography on a silica gel using 15% EtOAc/hexane to afford the desired product as yellow oil (170 mg, 35% yield). HRMS calcd. for C$_{18}$H$_{22}$N$_4$Cl$_1$:329.1533. Found: 329.1530 (M+H).

Part C: Suzuki Reaction: A mixture of above chloro compound (0.140 g, 0.43 mmol, fw=328), 2,4-dichlorobenzeneboronic acid (95 mg, 0.65 mmol, fw=190.81) in toluene (5.0 mL) was treated with 2M aq. Na$_2$CO$_3$ (2.0 mL) and EtOH (1 mL). The reaction mixture was degassed under vacuum and purged with nitrogen (repeated 3 times) and then added Pd(PPh$_3$)$_2$Cl$_2$ (18.5 mg, 0.005 mmol, fw=738.18). After the addition the reaction mixture was degassed under vacuum and purged with nitrogen (repeated 3 times). The resultant mixture was refluxed under nitrogen for 6 h. TLC (1:50 MeOH/CH$_2$Cl$_2$) showed two new spots at Rf=0.75 and 0.5 along with small amount of starting material spot at Rf=0.33. The reaction mixture was cooled to room temp and partitioned between 20 ml of 1:1 EtOAc/water. The aq. layer was extracted with EtOAc (2×15 mL), dried (MgSO$_4$) and concentrated in vacuum to afford yellow oil. The crude was purified by flash column chromatography on a silica gel using 10% EtOAc/hexane to afford the top spot as yellow solid (20 mg). Further elution of the column with 15% EtOAc/hexane gave desired product (bottom spot) as yellow oil (60 mg, 40% yield, 125–126° C.). Also recovered 27.5 mg of unreacted chloropyrazine derivative. Top spot was characterized as mono chloro derivative of Example 35. HRMS calcd. for C$_{24}$H$_{26}$N$_4$Cl$_1$:405.1846. Found: 405.1841 (M+H). Bottom spot desired product. HRMS calcd. for C$_{24}$H$_{25}$N$_4$Cl$_2$: 439.1456. Found: 439.1455 (M+H).

The compounds of examples 37 to 40 were prepared by following experimental conditions outlined in Example 36, hereinabove.

What is claimed is:

1. A compound of the Formula I:

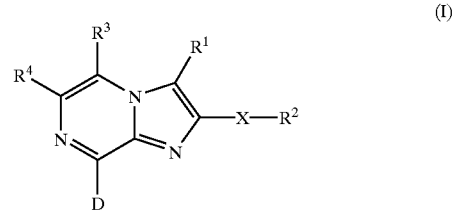

(I)

wherein:

X is CHR$^5$, NR$^5$, O, S, S(O)$_n$ or a single bond, wherein n is equal to 0, 1 or 2;

D is aryl or heteroaryl attached through an unsaturated carbon atom and wherein said aryl or heteroaryl is optionally substituted at any available position with from 1–5 of A$^1$, A$^2$, A$^3$, A$^4$ and A$^5$;

A$^1$, A$^2$, A$^3$, A$^4$ and A$^5$ are each independently H, C$_{1-6}$ alkyl, C$_{3-6}$ cycloalkyl, halo, C$_{1-4}$ haloalkyl, cyano, nitro, —OR$^{12}$, SH, —S(O)$_n$R$^{13}$, —COR$^{12}$, —CO$_2$R$^{12}$, —OC(O)R$^{13}$, —NR$^{11}$COR$^{12}$, —N(COR$^{12}$)$_2$, or —NR$^{11}$CONR$^{12}$R$^{14}$, or wherein A$^1$, A$^2$, A$^3$, A$^4$ and A$^5$ are each independently phenyl or phenyl substituted with from 1 to 4 of C$_{1-3}$ alkyl, C$_{1-3}$ alkoxy, halo, cyano, dimethylamino, CF$_3$, C$_2$F$_5$, OCF$_3$, SO$_2$Me or acetyl;

R$^1$ is C$_{1-10}$ alkyl, C$_{2-10}$ alkenyl, C$_{2-10}$ alkynyl, C$_{3-8}$ cycloalkyl, C$_{4-12}$ cycloalkylalkyl, NR$^6$R$^7$ or —C(R$^8$)(R$^9$)—O—R$^{10}$;

R$^2$ is C$_{1-4}$ alkyl or C$_{3-8}$ cycloalkyl, each of which is optionally substituted with from 1–3 hydroxy, halogen or C$_{1-4}$ alkoxy, or wherein when X is a bond, R$^2$ is CN, CF$_3$, or C$_2$F$_5$;

R$^3$ and R$^4$ are independently H, C$_{1-4}$ alkyl, C$_{2-4}$ alkenyl, C$_{2-4}$ alkynyl, C$_{3-5}$ cycloalkyl, C$_{1-4}$ alkoxy, C$_{1-4}$ haloalkyl, C$_{1-4}$ haloalkoxy, halogen, CN, or NR$^6$R$^7$;

R$^5$ is H, C$_{1-4}$ alkyl or C$_{3-8}$ cycloalkyl;

R$^6$ and R$^7$ are each independently H, C$_{1-4}$ alkyl, C$_{1-4}$ haloalkyl, C$_{2-8}$ alkoxyalkyl, C$_{3-6}$ cycloalkyl, C$_{4-12}$ cycloalkylalkyl, aryl, aryl(C$_{1-4}$ alkyl)-, heteroaryl or heteroaryl(C$_{1-4}$ alkyl)-;

R$^8$ and R$^9$ are each independently H or C$_{1-4}$ alkyl, or R$^8$ and R$^9$ are taken together as =CH$_2$;

R$^{10}$ is H or C$_{1-4}$ alkyl;

R$^{11}$ is H, C$_{1-4}$ alkyl, C$_{3-7}$ cycloalkyl, C$_{4-12}$ cycloalkylalkyl, phenyl or benzyl, each phenyl or benzyl optionally substituted on the aryl moiety with 1–3 groups of C$_{1-4}$ alkyl, halogen, C$_{1-4}$ haloalkyl, nitro, C$_{1-4}$ alkoxy, C$_{1-4}$ haloalkoxy, or dimethylamino; and, R$^{12}$, R$^{13}$ and R$^{14}$ are each independently H, C$_{1-6}$ alkyl, C$_{3-10}$ cycloalkyl, C$_{4-16}$ cycloalkylalkyl or C$_{1-4}$ haloalkyl.

2. The compound of claim 1, wherein X is a single bond.

3. The compound of claim 1, wherein D is phenyl.

4. The compound of claim 3 wherein the phenyl is

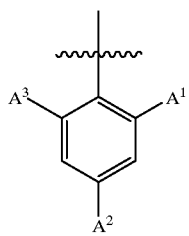

and wherein each of $A^1$, $A^2$ and $A^3$ is independently H, $C_{1-6}$ alkyl, $C_{1-6}$ alkoxy, halogen, $C_{1-4}$ haloalkyl or $OR^{12}$.

5. The compound of claim 4, wherein $A^1$ is H, $CH_3$ or Cl.

6. The compound of claim 4, wherein $A^2$ is Cl, —$OCH_3$ or —$OCHF_2$.

7. The compound of claim 4, wherein $A^3$ is H or $CH_3$.

8. The compound of claim 4, wherein:
$A^1$ is H, $CH_3$ or Cl;
$A^2$ is Cl, —$OCH_3$ or —$OCHF_2$ and $A^3$ is H or $CH_3$.

9. The compound of claim 1, wherein $R^1$ is —$C(R^8)(R^9)$—O—$R^{10}$.

10. The compound of claim 9, wherein each of $R^8$, $R^9$ and $R^{10}$ are independently H or $C_{1-4}$ alkyl.

11. The compound of claim 10, wherein $R^8$ is H.

12. The compound of claim 10, wherein $R^9$ is $C_2H_5$ or $C_3H_7$.

13. The compound of claim 10, wherein $R^{10}$ is H.

14. The compound of claim 10, wherein $R^8$ is H, $R^9$ is $C_2H_5$ or $C_3H_7$ and $R^{10}$ is H.

15. The compound of claim 1, wherein $R^2$ is unsubstituted C1–4 alkyl.

16. The compound of claim 15, wherein $R^1$ is $C_2H_5$.

17. The compound of claim 1, wherein each of $R^3$ and $R^4$ are H.

18. The compound of claim 1, wherein $R^1$ is —$C(R^8)(R^9)$—O—$R^{10}$, $R^2$ is unsubstituted $C_{1-4}$ alkyl, each of $R^3$ and $R^4$ is H, X is a single bond and D is phenyl of the formula

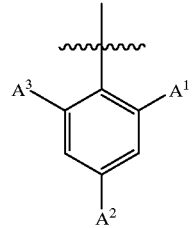

wherein $R^8$ is H, $R^9$ is $C_2H_5$ or $C_3H_7$, $R^{10}$ is H, each of $A^1$, is H, $A^2$ is Cl, —$OCH_3$ or —$OCHF_2$ and $A^3$ is H.

19. A pharmaceutical composition comprising a pharmaceutically acceptable carrier and a therapeutically effective amount of the compound of claim 1.

20. A method of treating a subject afflicted with anorexia nervosa comprising administering to said subject a therapeutically effective amount of a compound of claim 1.

21. A method of treating a subject afflicted with depression, wherein said depression is characterized by overexpression of CRF, comprising administering to said subject a therapeutically effective amount of a compound of claim 1.

22. A method of treating a subject afflicted with anxiety comprising administering to said subject a therapeutically effective amount of a compound of claim 1.

* * * * *